United States Patent
Cordier et al.

(10) Patent No.: US 10,512,485 B2
(45) Date of Patent: Dec. 24, 2019

(54) INTERPHALANGEAL ARTHRODESIS IMPLANT

(71) Applicants: FOURNITURES HOSPITALIERES INDUSTRIE, Quimper (FR); FH ORTHOPEDICS, Heimsbrunn (FR); Xavier Roussignol, Deville les Rouen (FR); Gérard Polle, Bois-Guillaume (FR); Julien Laborde, Toulouse (FR); Jean-Pierre Etchevers, Ascain (FR); Véronique Darcel, Bordeaux (FR); Guillaume Cordier, Aygurmorte les Graves (FR); François-Xavier Sevestre, Rennes (FR); Thibault De Rouvray, Saint Cyr sur Loire (FR)

(72) Inventors: Guillaume Cordier, Ayguemorte les Graves (FR); Véronique Darcel, Bordeaux (FR); Jean-Pierre Etchevers, Ascain (FR); Julien Laborde, Toulouse (FR); Gérard Polle, Bois-Guillaume (FR); Xavier Roussignol, Deville les Rouen (FR); Guillaume Rouyer, Quimper (FR); François-Xavier Sevestre, Rennes (FR); Thibault De Rouvray, Saint Cyr sur Loire (FR)

(73) Assignee: FOURNITURES HOSPITALIERES INDUSTRIE, Quimper (FR)

( * ) Notice: Subject to any disclaimer, the term of this patent is extended or adjusted under 35 U.S.C. 154(b) by 0 days.

(21) Appl. No.: 15/599,789

(22) Filed: May 19, 2017

(65) Prior Publication Data
US 2017/0333081 A1 Nov. 23, 2017

(30) Foreign Application Priority Data

May 19, 2016 (FR) ...................... 16 54466

(51) Int. Cl.
| | |
|---|---|
| A61B 17/72 | (2006.01) |
| A61B 17/68 | (2006.01) |
| A61B 17/86 | (2006.01) |
| A61F 2/42 | (2006.01) |
| A61F 2/46 | (2006.01) |
| A61F 2/30 | (2006.01) |

(52) U.S. Cl.
CPC .............. *A61B 17/68* (2013.01); *A61B 17/86* (2013.01); *A61F 2/4225* (2013.01);
(Continued)

(58) Field of Classification Search
CPC ............... A61B 17/7291; A61B 17/681; A61F 2002/4228; A61F 2/42
See application file for complete search history.

(56) References Cited

U.S. PATENT DOCUMENTS 6,458,134 B1 * 10/2002 Songer .................. A61B 17/68
606/304
6,475,242 B1 * 11/2002 Bramlet ............. A61B 17/1659
623/21.11
(Continued)

FOREIGN PATENT DOCUMENTS

| FR | 3018441 A1 | 9/2015 |
| WO | 2016027025 A2 | 2/2016 |

OTHER PUBLICATIONS

English Translation of FR3018441.

*Primary Examiner* — Jacqueline T Johanas
(74) *Attorney, Agent, or Firm* — Cantor Colburn LLP

(57) ABSTRACT

This interphalangeal arthrodesis implant comprises a proximal anchor portion intended to be engaged and anchored in the medullary canal of a first phalanx sectioned along a first osteotomy plane, the proximal anchor portion including a plurality of proximal anchor branches each provided with at least one bone anchor element; and a distal anchor portion, connected to the proximal anchor portion, intended to be engaged and anchored in the medullary canal of a second
(Continued)

phalanx sectioned along a second osteotomy plane, the distal anchor portion including a plurality of distal anchor branches each provided with at least one bone anchor element. The distal anchor portion comprises a stop portion including a stop surface intended to bear against a sectioned surface of the first phalanx extending along the first osteotomy plane.

11 Claims, 3 Drawing Sheets

(52) U.S. Cl.
CPC ........ *A61F 2/4606* (2013.01); *A61B 17/7291* (2013.01); *A61B 2017/681* (2013.01); *A61F 2/42* (2013.01); *A61F 2002/30136* (2013.01); *A61F 2002/30777* (2013.01); *A61F 2002/30904* (2013.01); *A61F 2002/4228* (2013.01)

(56) References Cited

U.S. PATENT DOCUMENTS

| | | | |
|---|---|---|---|
| 9,283,007 B2* | 3/2016 | Augoyard | A61B 17/68 |
| 9,492,215 B2* | 11/2016 | Augoyard | A61B 17/68 |
| 9,545,274 B2* | 1/2017 | McCormick | A61B 17/7291 |
| 10,022,167 B2* | 7/2018 | Augoyard | A61B 17/68 |
| 2003/0130660 A1* | 7/2003 | Levy | A61B 17/7266 606/63 |
| 2008/0132894 A1* | 6/2008 | Coilard-Lavirotte | A61B 17/1604 606/60 |
| 2008/0177262 A1 | 7/2008 | Augoyard et al. | |
| 2011/0082508 A1* | 4/2011 | Reed | A61B 17/7225 606/329 |
| 2013/0090655 A1* | 4/2013 | Tontz | A61B 17/7233 606/64 |
| 2014/0018930 A1* | 1/2014 | Oster | A61F 2/4261 623/21.12 |
| 2014/0180428 A1* | 6/2014 | McCormick | A61F 2/4225 623/21.19 |
| 2014/0188179 A1* | 7/2014 | McCormick | A61B 17/7291 606/301 |
| 2014/0309747 A1* | 10/2014 | Taylor | A61F 2/42 623/21.11 |
| 2015/0073413 A1 | 3/2015 | Palmer et al. | |
| 2015/0223849 A1* | 8/2015 | McCormick | A61B 17/7291 606/63 |
| 2015/0374503 A1* | 12/2015 | Lovick | A61B 17/7291 623/23.5 |
| 2016/0317198 A1* | 11/2016 | Fox | A61B 17/7225 |
| 2017/0239059 A1* | 8/2017 | Boublil | A61F 2/4225 |
| 2017/0319349 A1* | 11/2017 | Kowalczyk | A61B 17/7291 |

* cited by examiner

INTERPHALANGEAL ARTHRODESIS IMPLANT

CROSS REFERENCE TO RELATED APPLICATIONS

This application claims priority under 35 U.S.C. 119 to the following French Patent Application No. 16/54466 filed on May 19, 2016, the contents of which are incorporated herein by reference thereto.

BACKGROUND

The present invention concerns an interphalangeal arthrodesis implant intended to allow a bone fusion between a first and a second phalanxes of an interphalangeal joint, such as an interphalangeal joint of a foot, and in particular a proximal interphalangeal articulation of a foot.

It happens that a foot having a hallux valgus, that is to say a deformation corresponding to a varus deviation of the first metatarsal and a valgus deviation of the big toe, also has a deformation of the second toe or even of the third toe. Indeed, under the influence of the big toe, the second toe, and possibly the third toe, can deform and take a shape of claw.

Some deformations of the second and third toes require a surgical intervention intended to give a normal aspect to the foot, and to eliminate the pain induced by these deformations. Such a surgical intervention can consist of an interphalangeal arthrodesis between the first and second phalanxes of the second toe, and possibly an interphalangeal arthrodesis between the first and second phalanxes of the third toe, so as to immobilize the concerned joint(s) in order to eliminate the patient's pain.

An interphalangeal arthrodesis generally consists in:
performing an osteotomy of the first and second phalanxes on either side of the concerned joint and along a first and a second osteotomy planes extending respectively perpendicularly to the first and second phalanxes,
providing an interphalangeal arthrodesis implant comprising a proximal anchor portion, and a distal anchor portion connected to the proximal anchor portion,
machining the medullary canal of the first phalanx and the medullary canal of the second phalanx so that they have dimensions corresponding substantially to the outer dimensions of the proximal and distal anchor portions,
inserting and anchoring the proximal anchor portion in the medullary canal of the first phalanx previously sectioned along the first osteotomy plane, and
inserting and anchoring the distal anchor portion in the medullary canal of the second phalanx previously sectioned along the second osteotomy plane, so that the sectioned surfaces of the first and second phalanxes substantially bear against one another.

In a known manner, the proximal and distal anchor portions of the interphalangeal arthrodesis implant can respectively include a plurality of proximal anchor branches each provided with at least one bone anchor element, and a plurality of distal anchor branches each provided with at least one bone anchor element.

However, such a configuration of the interphalangeal arthrodesis implant can induce, during insertion of the distal anchor portion in the medullary canal of the second phalanx, a displacement of the proximal anchor portion relative to the first phalanx, and more particularly a depression of the proximal anchor portion in the medullary canal of the first phalanx beyond its predetermined position. Such a depression of the implant can impair the final anchoring of the distal anchor portion in the second phalanx, and therefore require a possible subsequent resumption of the interphalangeal arthrodesis implant by the surgeon.

BRIEF SUMMARY

The present invention aims to overcome this disadvantage.

The technical problem at the basis of the invention therefore consists in providing an interphalangeal arthrodesis implant which ensures an easy and reliable fastening of two sectioned phalanxes of an interphalangeal joint.

For this purpose, the present invention concerns an interphalangeal arthrodesis implant intended to allow a bone fusion between a first and a second phalanxes of an interphalangeal joint, the interphalangeal arthrodesis implant comprising:
a proximal anchor portion intended to be engaged and anchored in the medullary canal of the first phalanx previously sectioned along a first osteotomy plane, the proximal anchor portion including a plurality of proximal anchor branches each provided with at least one bone anchor element,
a distal anchor portion connected to the proximal anchor portion, intended to be engaged and anchored in the medullary canal of the second phalanx previously sectioned along a second osteotomy plane, the distal anchor portion including a plurality of distal anchor branches each provided with at least one bone anchor element, the distal anchor portion comprising a stop portion including a stop surface intended to bear against a sectioned surface of the first phalanx extending along the first osteotomy plane,
wherein each proximal anchor branch includes a first end and a second end opposite the respective first end, the first end of each proximal anchor branch being closer to the distal anchor portion than the respective second end, and each distal anchor branch includes a first end and a second end opposite the respective first end, the first end of each distal anchor branch being closer to the proximal anchor portion than the respective second end,
wherein the proximal anchor portion includes a proximal end portion connecting the second ends of the proximal anchor branches, and the distal anchor portion includes a distal end portion connecting the second ends of the distal anchor branches.

Such a configuration of the interphalangeal arthrodesis implant, and more particularly the presence of the bearing surface, allows to limit the depth of depression of the proximal anchor portion in the medullary canal of the respective phalanx, and therefore to avoid an inappropriate subsequent anchoring of the distal anchor portion on the respective phalanx. These dispositions thus allow to ensure an easy and reliable fastening of two phalanxes of an interphalangeal joint.

It should be noted that the distal and proximal anchor branches give the implant some elasticity guaranteeing an optimal anchoring of the distal and proximal anchor portions in the respective medullary canals. In addition, the presence of anchor elements on the distal and proximal anchor branches increases the stability (in particular in rotation and in translation) of the implant, and therefore ensures rapid and optimal bone consolidation.

The interphalangeal arthrodesis implant can further have one or more of the following characteristics, taken alone or in combination.

According to an embodiment of the invention, the proximal anchor portion extends generally along a first axis of extension, and the distal anchor portion extends generally along a second axis of extension.

According to an embodiment of the invention, the first and second axes of extension being inclined relative to each other. The first and second axes of extension can, for example, be inclined relative to each other by an angle comprised between 3° and 15°.

According to an embodiment of the invention, the proximal anchor branches are distributed, advantageously regularly distributed, around the first axis of extension, and the distal anchor branches are distributed, advantageously regularly distributed, around the second axis of extension.

According to an embodiment of the invention, the stop surface is substantially planar.

According to an embodiment of the invention, the stop surface extends in an inclined manner relative to the axis of extension of the proximal anchor portion.

According to an embodiment of the invention, the stop surface is annular, and can, for example, extend coaxially with the second axis of extension.

According to an embodiment of the invention, the stop surface is formed by a shoulder, and for example by an annular shoulder.

According to an embodiment of the invention, the proximal anchor portion further includes a connecting portion connecting the stop portion and the proximal anchor branches.

According to an embodiment of the invention, the connecting portion has a substantially smooth outer surface.

According to an embodiment of the invention, the connecting portion has a substantially circular cross section.

According to an embodiment of the invention, the first ends of the proximal anchor branches are connected to the connecting portion, and the first ends of the distal anchor branches are connected to the stop portion.

According to an embodiment of the invention, the proximal anchor branches extend from the connecting portion, and the distal anchor branches extend from the stop portion.

According to an embodiment of the invention, the proximal and distal anchor branches each have a generally elongated shape, and in which the proximal anchor branches converge substantially in the direction of the proximal end portion and the distal anchor branches converge substantially in the direction of the distal end portion.

According to an embodiment of the invention, the proximal and distal end portions each have a generally bullet shape.

According to an embodiment of the invention, the interphalangeal arthrodesis implant is formed in one piece.

According to an embodiment of the invention, each proximal and distal anchor branch includes a plurality of anchor elements disposed along the respective anchor branch.

According to an embodiment of the invention, each anchor element is an anchor notch.

According to an embodiment of the invention, the interphalangeal arthrodesis implant is radiotransparent.

According to an embodiment of the invention, the interphalangeal arthrodesis implant is made of plastic material, such as polymer.

According to an embodiment of the invention, the interphalangeal arthrodesis implant is made of PEEK.

According to an embodiment of the invention, the proximal end portion includes a substantially planar proximal end face and extending transversely, and for example perpendicularly, to the first axis of extension, and the distal end portion includes a substantially planar distal end face and extending transversely, and for example perpendicularly, to the second axis of extension.

BRIEF DESCRIPTION OF THE DRAWINGS

In any case, the invention will be well understood using the following description with reference to the appended schematic drawing showing, by way of non-restrictive example, an embodiment of this interphalangeal arthrodesis implant.

BRIEF DESCRIPTION

Figure 1:
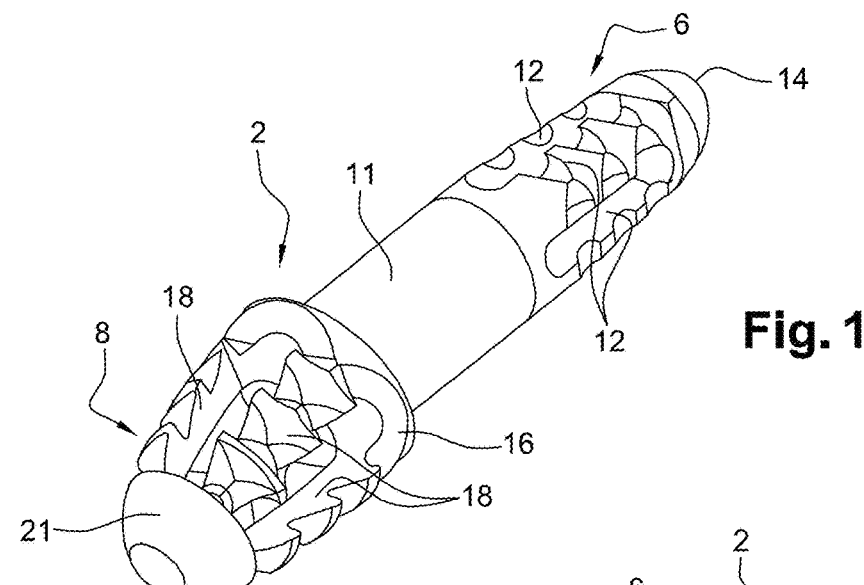
FIG. 1 is a perspective view of an interphalangeal arthrodesis implant according to the present invention.
Figure 2:
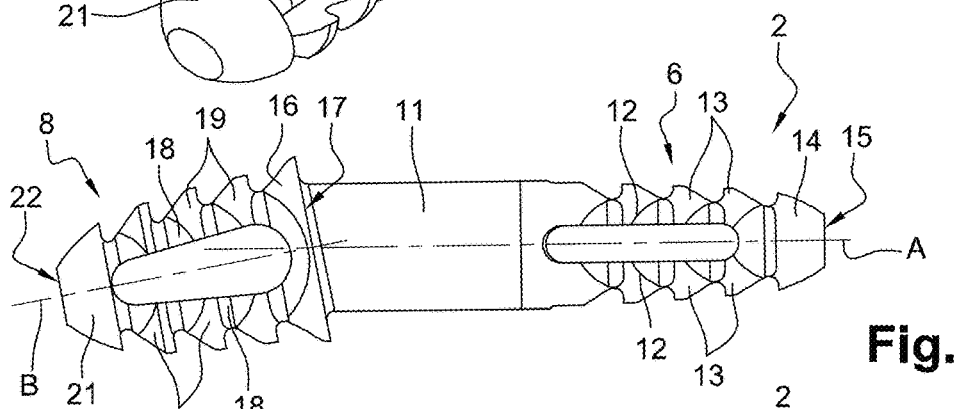
FIGS. 2 and 3 are respectively side and top views of the interphalangeal arthrodesis implant of FIG. 1.
Figure 3:
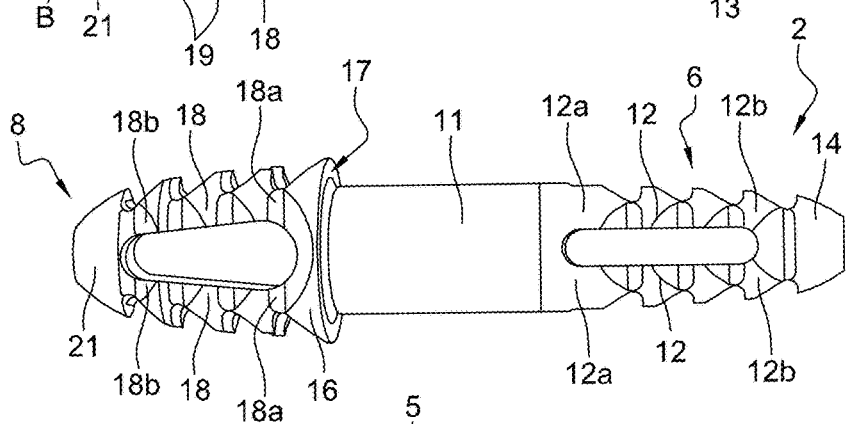
Figure 4:
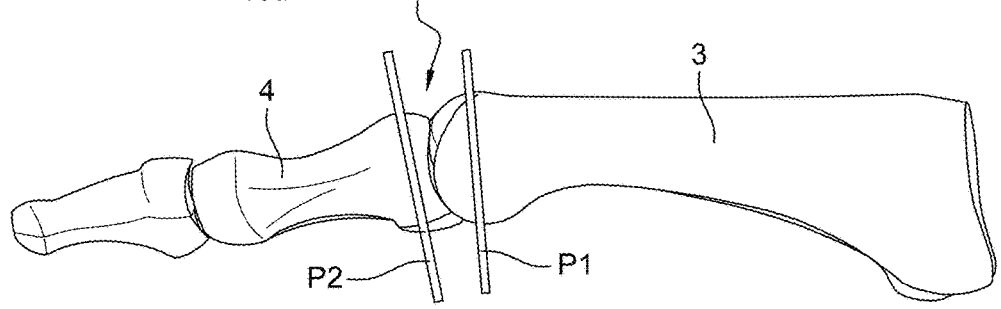
FIG. 4 is a side view of a second toe of a foot, schematizing first and second osteotomy planes respectively of the first and second phalanxes of the proximal interphalangeal joint of the second toe.
Figure 5:
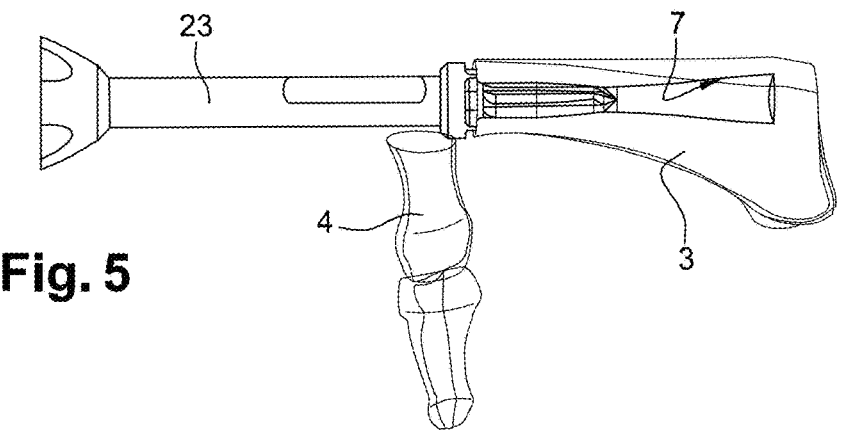
FIGS. 5 and 6 are views showing steps of machining the medullary canals of the first and second phalanxes of FIG. 4.
Figure 6:
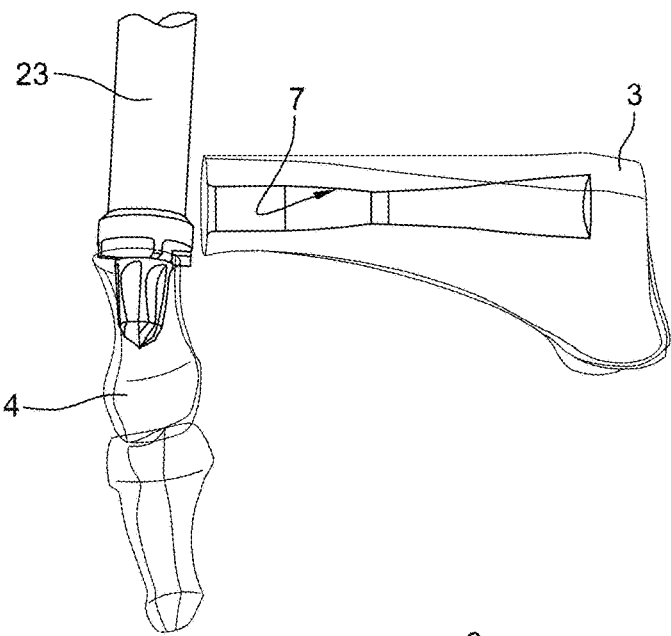
Figure 7:
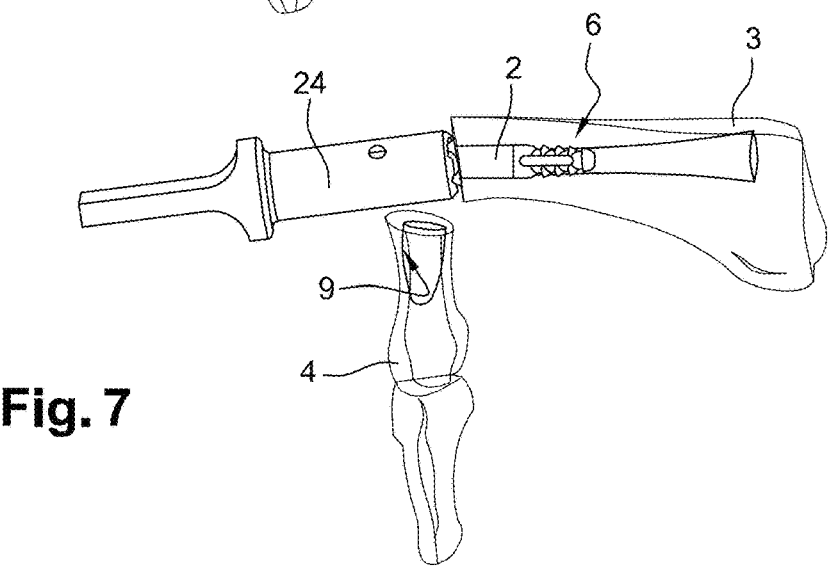
FIGS. 7 to 9 are views showing different steps of fastening the interphalangeal arthrodesis implant of FIG. 1 in the first and second phalanxes of FIG. 4.
Figure 8:
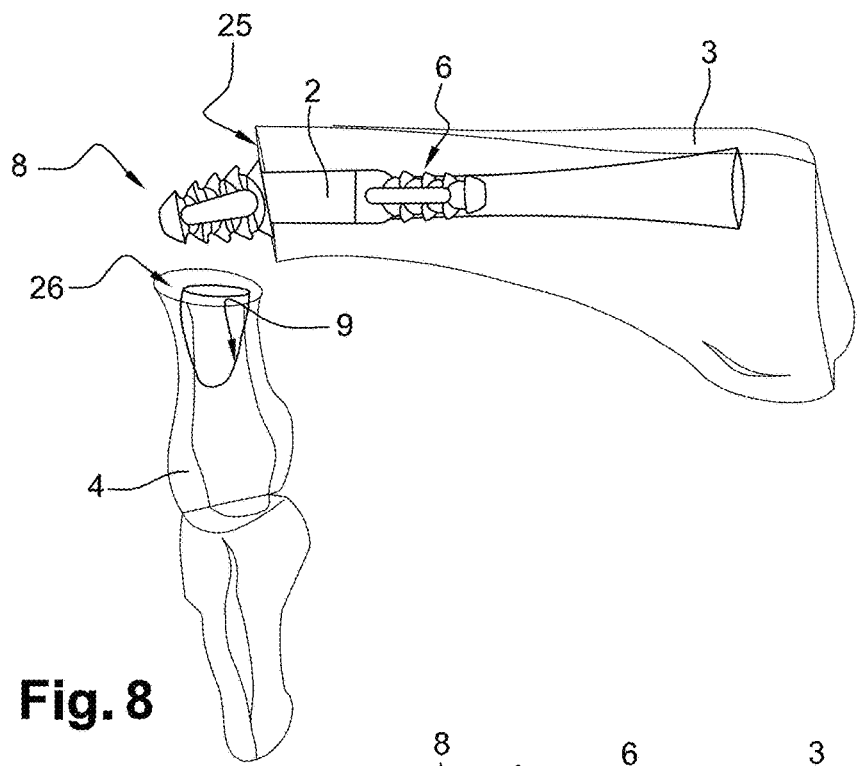
Figure 9:
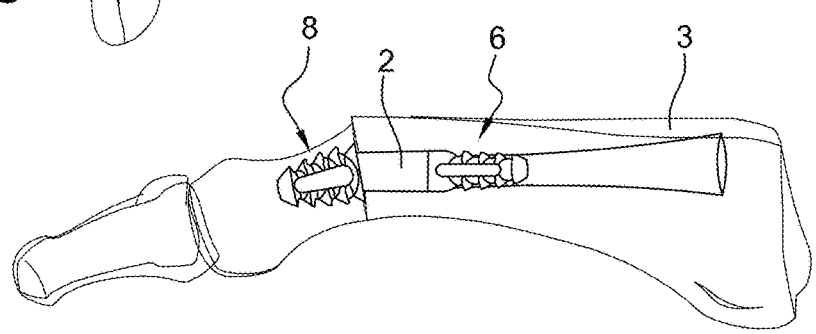

FIGS. 1 to 3 show an interphalangeal arthrodesis implant 2 intended to allow a bone fusion between a first and a second phalanxes 3, 4 of a proximal interphalangeal joint 5 of a foot. The interphalangeal arthrodesis implant 2 is advantageously formed in one piece, and can be made, for example, of plastic material, such as PEEK.

The interphalangeal arthrodesis implant 2 comprises a proximal anchor portion 6 intended to be engaged and anchored in the medullary canal 7 of the first phalanx 3 previously sectioned along a first osteotomy plane P1, and a distal anchor portion 8 intended to be engaged and anchored in the medullary canal 9 of the second phalanx 4 previously sectioned along a second osteotomy plane P2.

The proximal anchor portion 6 has a generally elongated shape, and extends generally along a first axis of extension A. The proximal anchor portion 6 includes a connecting portion 11 connected to the distal anchor portion 8 and extending along the first axis of extension A. According to the embodiment shown in Figures, the connecting portion 11 has a smooth outer surface and a circular cross section.

The proximal anchor portion 6 further includes a plurality of proximal anchor branches 12, for example four, regularly distributed around the first axis of extension A. Each proximal anchor branch 12 has a generally elongated shape and includes a first end 12a connected to the connecting portion 11 and a second end 12b opposite the respective first end 12a. Thus, each proximal anchor branch 12 extends from the connecting portion 11.

Each proximal anchor branch 12 is advantageously provided with a plurality of bone anchor notches 13 disposed along the respective proximal anchor branch 12.

The proximal anchor portion 6 also includes a proximal end portion 14 connecting the second ends 12b of the proximal anchor branches 12. According to the embodiment shown in Figures, the proximal end portion 14 has a generally bullet shape and includes a planar proximal end face 15 and extending perpendicularly to the first axis of extension A.

The distal anchor portion 8 has generally an elongated shape and extends generally along a second axis of extension B inclined relative to the first axis of extension A by an angle comprised, for example, between 3° and 15°.

The distal anchor portion 8 includes a stop portion 16 including a stop surface 17 intended to bear against a sectioned surface of the first phalanx 3. It should be noted that the connecting portion 11 is configured to connect the stop portion 16 and the proximal anchor branches 12.

According to the embodiment shown in the figures, the stop surface 17 is formed by a shoulder configured so that the stop portion 16 has an external diameter greater than the external diameter of the connecting portion 11. Advantageously, the stop surface 17 is annular and extends coaxially with the second axis of extension. According to the embodiment shown in the figures, the stop surface 17 is planar and extends in an inclined manner relative to the first axis of extension A.

The distal anchor portion 8 further includes a plurality of distal anchor branches 18, for example four, regularly distributed around the second axis of extension B. Each distal anchor branch 18 has a generally elongated shape and includes a first end 18a connected to the stop portion 16 and a second end 18b opposite the respective first end 18a. Thus, each distal anchor branch 18 extends from the stop portion 16.

Each distal anchor branch 18 is advantageously provided with a plurality of bone anchor notches 19 disposed along the respective distal anchor branch 18.

The distal anchor portion 8 also includes a distal end portion 21 connecting the second ends 18b of the distal anchor branches 18. According to the embodiment shown in Figures, the distal end portion 21 has a generally bullet shape and includes a planar distal end face 22 and extending perpendicularly to the second axis of extension B.

According to the embodiment shown in Figures, the proximal anchor branches 12 converge substantially in the direction of the distal end portion 14 and the distal anchor branches 18 converge substantially in the direction of the distal end portion 21.

A method for correcting a deformation of the second toe of a patient suffering from a hallux valgus using an interphalangeal arthrodesis implant 2 according to the present invention will now be described, by referring more particularly to FIGS. 4 to 9.

Such a correction method comprises the steps consisting in:
  performing an osteotomy of the first and second phalanxes 3, 4 of the second toe on either side of the proximal interphalangeal joint and along a first and second osteotomy planes P1, P2 respectively extending substantially perpendicularly to the first and second phalanxes 3, 4 (see FIG. 4),
  machining, using a conformation tool 23, the medullary canal 7 of the first phalanx 3 and the medullary canal 9 of the second phalanx 4 such that they have dimensions corresponding substantially to the outer dimensions of the proximal and distal anchor portions 6, 8 of the interphalangeal arthrodesis implant 2 (see FIGS. 5 and 6),
  inserting and anchoring, using a gripping tool 24, the proximal anchor portion 6 in the medullary canal 7 of the first phalanx 3 previously sectioned along the first osteotomy plane P1, so that the stop surface 17 bears against the sectioned surface 25 of the first phalanx 3 extending along the first osteotomy plane P1 (see FIGS. 7 and 8),
  inserting and anchoring the distal anchor portion 8 in the medullary canal 9 of the second phalanx 4 previously sectioned along the second osteotomy plane P2, so that the sectioned surfaces 25, 26 of the first and second phalanxes 3, 4 bear against one another.

Figure 10:
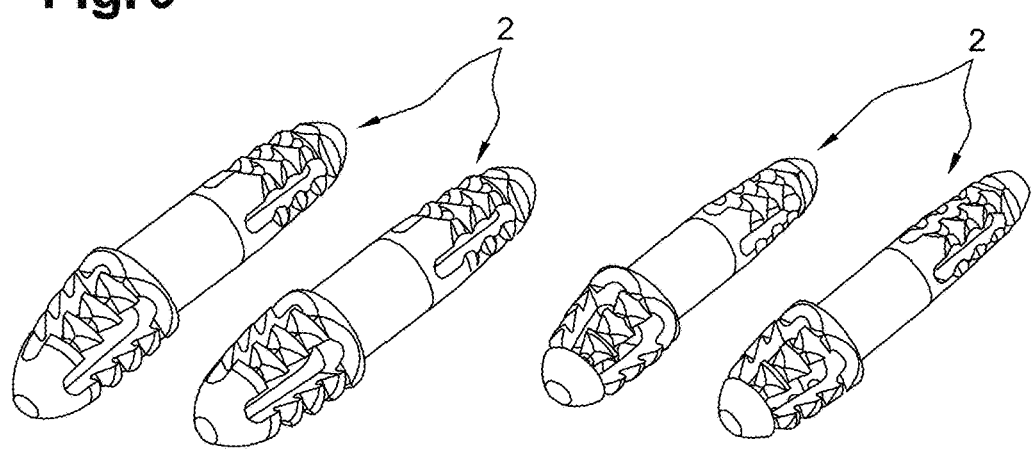
FIG. 10 is a perspective view of a range of interphalangeal arthrodesis implants according to the present invention.

As shown in FIG. 10, the interphalangeal arthrodesis implant 2 can be declined, for example, in two angulations, that is to say in two values of the angle of inclination between the first and second axes of extension A, B, and in two sizes. Such a declination of the interphalangeal arthrodesis implant 2 allows forming a range of implants comprising four different implants. However, the interphalangeal arthrodesis implant 2 could be declined in more than two angulations, for example in three or four different angulations, and in more than two sizes, for example in three or four different sizes, in order to respond to the different anatomies which can be encountered.

It goes without saying that the invention is not limited to the sole embodiment of this interphalangeal arthrodesis implant, described above by way of example, but it embraces, on the contrary, all the variants.

What is claimed is:
1. An interphalangeal arthrodesis implant intended to allow a bone fusion between a first and a second phalanxes of an interphalangeal joint, the interphalangeal arthrodesis implant being made in one piece and comprising:
  a proximal anchor portion intended to be engaged and anchored in a medullary canal of the first phalanx previously sectioned along a first osteotomy plane (P1), the proximal anchor portion including a plurality of proximal anchor branches each provided with at least one bone anchor element and each proximal anchor branch having a generally elongated shape, the proximal anchor branches being separate and distinct from each other, the proximal anchor portion including a plurality of proximal longitudinal slots angularly offset and defining the plurality of proximal anchor branches, the plurality of proximal anchor branches defining a hollow proximal channel in which emerges each of the proximal longitudinal slots,
  a distal anchor portion, connected to the proximal anchor portion, intended to be engaged and anchored in a medullary canal of the second phalanx previously sectioned along a second osteotomy plane (P2), the distal anchor portion including a plurality of distal anchor branches each provided with at least one bone anchor element and each distal anchor branch having a generally elongated shape, the distal anchor branches being separate and distinct from each other, the distal anchor portion including a plurality of distal longitudinal slots angularly offset and defining the plurality of distal anchor branches, the plurality of distal anchor branches defining a hollow distal channel in which emerges each of the distal longitudinal slots, the distal anchor portion comprising a stop portion including a stop surface intended to bear against a sectioned surface of the first phalanx extending along the first osteotomy plane (P1),
  wherein each proximal anchor branch includes a first end and a second end opposite the respective first end, the first end of each proximal anchor branch being closer to the distal anchor portion than the respective second end and the first end of each proximal anchor branch being spaced from a first axis of extension (A) of the proximal anchor portion by a first proximal distance and the second end of each proximal anchor branch being spaced from the first axis of extension (A) of the proximal anchor portion by a second proximal distance, the first proximal distance being greater than the second proximal distance, and each distal anchor branch includes a first end and a second end opposite to the respective first end, the first end of each distal anchor branch being closer to the proximal anchor portion than the respective second end and the first end of each distal anchor branch being spaced from a second axis of extension (B) of the distal anchor portion by a first distal distance and the second end of each distal anchor branch being spaced from the second axis of extension (B) of the distal anchor portion by a second distal distance, the first distal distance being greater than the second distal distance, wherein the proximal anchor portion includes a proximal end portion connecting the second ends of the proximal anchor branches, and the distal anchor portion includes a distal end portion connecting the second ends of the distal anchor branches, the proximal anchor branches converging inwardly towards each other in the direction of the proximal end portion as they extend from their respective first end towards their respective second end and the distal anchor branches converging inwardly towards each other in the direction of the distal end portion as they extend from their respective first end towards their respective second end.

2. The interphalangeal arthrodesis implant according to claim 1, wherein the stop surface is substantially planar.

3. The interphalangeal arthrodesis implant according to claim 1, wherein the stop surface is annular.

4. The interphalangeal arthrodesis implant according to claim 1, wherein the proximal anchor portion extends generally along the first axis of extension (A), and the distal anchor portion extends generally along the second axis of extension (B).

5. The interphalangeal arthrodesis implant according to claim 4, wherein the first and second axes of extension (A, B) are inclined relative to one another.

6. The interphalangeal arthrodesis implant according to claim 4, wherein the proximal anchor branches are distributed around the first axis of extension (A), and the distal anchor branches are distributed around the second axis of extension (B).

7. The interphalangeal arthrodesis implant according to claim 1, wherein the proximal anchor portion further includes a connecting portion connecting the stop portion and the proximal anchor branches.

8. The interphalangeal arthrodesis implant according to claim 7, wherein the connecting portion has a substantially smooth outer surface.

9. The interphalangeal arthrodesis implant according to claim 7, wherein the connecting portion has a substantially circular cross section.

10. The interphalangeal arthrodesis implant according to claim 7, wherein the first ends of the proximal anchor branches are connected to the connecting portion, and the first ends of the distal anchor branches are connected to the stop portion.

11. The interphalangeal arthrodesis implant according to claim 1, wherein the proximal and distal end portions each have a generally bullet shape.

* * * * *